United States Patent [19]

Hsich et al.

[11] Patent Number: 5,998,149

[45] Date of Patent: Dec. 7, 1999

[54] METHOD OF DETECTING TRANSMISSIBLE SPONGIFORM ENCEPHALOPATHIES

[75] Inventors: Gary Hsich, Philadelphia, Pa.; Kimbra Kenney, Arlington, Va.; Clarence J. Gibbs, Washington, D.C.; Michael G. Harrington, La Canada, Calif.

[73] Assignee: The United States of America as represented by the Department of Health and Human Services, Washington, D.C.

[21] Appl. No.: 08/630,961

[22] Filed: Apr. 5, 1996

[51] Int. Cl.⁶ ............................ G01N 33/53; G01N 1/00; A61K 49/04
[52] U.S. Cl. .................................. 435/7.1; 424/2; 424/5; 435/7.92; 435/7.93; 436/149; 436/811
[58] Field of Search ..................................... 435/7.1, 7.92, 435/7.93, 5; 424/2; 436/149, 811

[56] References Cited

U.S. PATENT DOCUMENTS 4,892,814  1/1990  Harrington et al. ...................... 435/5
5,270,165  12/1993  Van Nostrand et al. ................ 435/7.1

OTHER PUBLICATIONS

Ichimura et al "Widespread Distributuion of the 14–3–3 Protein in Vertibrate Brains and Bovine Tissues: Correlation with the Distribution of Calcium–Dependent Protein Kinases" J. Neurchem 56:1449–1541 (1991).

*Primary Examiner*—James C. Housel
*Assistant Examiner*—Rodney P. Swartz
*Attorney, Agent, or Firm*—Townsend and Townsend and Crew LLP

[57] ABSTRACT

This invention provides an improved assays for the detection of transmissible spongiform encephalopathies (TSEs) in humans and non-human mammals. The methods involve detecting the presence or absence of 14-3-3 proteins in cerebrospinal fluid from the tested organism. Elevated levels of 14-3-3 are indicative of transmissible spongiform encephalopathies, in particular Creutzfeldt-Jacob disease in humans or mad cow disease in bovines).

10 Claims, 1 Drawing Sheet

METHOD OF DETECTING TRANSMISSIBLE
SPONGIFORM ENCEPHALOPATHIES

BACKGROUND OF THE INVENTION

The transmissible spongiform encephalopathies (TSE) constitute a group of neurodegenerative diseases. In humans these diseases include Creutzfeldt-Jakob disease (CJD), Gerstmann-Straussler-Scheinker syndrome, Fatal Familial Insomnia, and Kuru (see, e.g., *Harrison's Principles of Internal Medicine*, Isselbacher et al., eds., McGraw-Hill, Inc. New York, (1994); Medori et al. 1992 *N. Engl. J. Med.*, 326: 444–9.). In animals the TSE's include sheep scrapie, bovine spongiform encephalopathy, transmissible mink encephalopathy, and chronic wasting disease of captive mule deer and elk (Gajdusek, (1990) *Subacute Spongiform Encephalopathies: Transmissible Cerebral Amyloidoses Caused by Unconventional Viruses*. Pp. 2289–2324 In: *Virology*, Fields, ed. New York: Raven Press, Ltd.). Transmissible spongiform encephalopathies are characterized by the same hallmarks: a spongiform degeneration, reactive gliosis in the cortical and subcortical gray matters of the brain, and transmission when experimentally inoculated into laboratory animals including primates, rodents, and transgenic mice.

Recently, the rapid spread of bovine spongiform encephalopathy and its correlation with elevated occurrence of spongiform encephalophathies in humans has lead to a significant increase of interest in the detection of transmissible spongiform encephalopathies in non-human mammals. The tragic consequences of accidental transmission of these diseases (see, e.g., Gajdusek, *Infectious Amyloids*, and Prusiner *Prions In Fields Virology*. Fields, et al., eds. Lippincott-Ravin, Pub. Philadelphia (1996); Brown et al. (1992) *Lancet*, 340: 24–27), and the decontamination difficulties (Asher et al. (1986) pages 59–71 In: *Laboratory Safety: Principles and Practices*, Miller ed. Am. Soc. Microb.), and recent concern about bovine spongiform encephalopathy (*British Med. J.* 1995; 311: 1415–1421) underlie the urgency of having a diagnostic test that would identify humans and animals with transmissible spongiform encephalopathies.

Definitive premortem diagnosis of these transmissible diseases can only be made histopathologically; however, biopsy of brain tissue is not an ideal method due to risks to animals, patients, and health care personnel. Moreover, lesions can be missed because of the patchy nature of the pathological process.

Measurement of most cerebrospinal fluid (CSF) proteins that have been implicated as pre-mortem markers of Creutzfeldt-Jakob disease have not been very useful diagnostically. These include neuron-specific enolase (NSE) (Jimi et al. (1992) *Lancet*, 211: 37–46; and Zer et al. (1995) *Lancet*, 345: 160-9-1610), S-100b protein (Jimi et al., supra), brain-type isozyme of creatine kinase (Jimi et al., supra), GTP binding protein G0 (Jimi et al., supra), ubiquitin (Manaka et al. (1992) *Neurosci. Letts.* 139: 47–49), and lactic acid (Awerbuch et al. (1985) *Internat. J. Neurosci.*, 42: 1–5).

However, two useful marker proteins, designated proteins 130 and 131, were discovered by two-dimensional electrophoresis (2DE) and silver staining surveys of cerebrospinal fluid (CSF) (see, e.g., Harrington et al. (1986) *N. Engl. J. Med.*, 315: 279–283 and U.S. Pat. No. 4,892,814). These markers were shown to have very high sensitivity (21/21) and specificity (515/520) in the diagnosis of Creutzfeldt-Jacob disease, and this test has been extremely useful in the premortem diagnosis of several difficult cases (see, e.g., Croxson et al. (1988) *Neurology* 38: 1128–30; Blisard et al. (1990) *J. Neurological Sci.*, 99: 75-81; Marzewski et al., (1988) *Neurology*, 38: 1131–33; Macario et al. (1991) *British Med. J.* 302: 1149). The only other disease in which these proteins were found was herpes encephalitis which is easily distinguished on clinical presentation. Testing for these markers, however, has required the two-dimensional electrophoresis (2DE) technique, which is cumbersome and time-consuming. Thus, despite the very high correlation of these marker proteins with the disease, the two-dimensional electrophoresis biochemical test has not become practical for clinical use.

SUMMARY OF THE INVENTION

This invention provides improved assays for the detection of transmissible spongiform encephalopathies (TSEs) in humans and non-human mammals. The invention is premised, in part, on the surprising discovery that elevated levels of 14-3-3 protein(s) it cerebrospinal fluid are indicative of (highly correlated with) transmissible spongiform encephalopathies (e.g., Creutzfeldt-Jacob disease in humans and bovine spongiform encephalopathy (mad cow disease) in bovines).

In a preferred embodiment this invention provides a method of detecting a transmissible spongiform encephalopathy (TSE) in a human or in a non-human mammal. Preferred transmissible spongiform encephalopathies include Creutzfeldt-Jakob Disease in the case of a human, bovine spongiform encephalopathy (BSE or mad cow disease) in the case of a bovine, and scrapie in the case of sheep.

The methods of this invention involve detecting the presence or absence, or quantifying, a 14-3-3 protein in cerebrospinal fluid of the human or non-human mammal. In the case of a human, detection of the 14-3-3 protein is preferably by use of an immunoassay (e.g., Western Blot assay or Sandwich assay). In the case of a non-human mammal, detection is by any convenient means, preferably a two-dimensional electrophoresis or by use of an immune assay (e.g., Western Blot assay or Sandwich assay). When applied to a human, the method can further comprise determining that the human does not suffer from herpes simplex encephalitis.

Preferred immunoassays use an anti-14-3-3 antibody. The antibody can be polyclonal or monoclonal, with polyclonal antibodies being more preferred. Particularly preferred assay formats include Western Blot assays and antigen capture (e.g., Sandwich) assays.

DEFINITIONS

The following definitions are set forth to illustrate and define the meaning and scope of the various terms used to describe the invention herein.

The term "14-3-3 protein" is used herein to refer to members of the 14-3-3 class of proteins as it is commonly known to those of skill in the art (see, e.g., Ichimura et al. (1988) *Proc. Nat'l. Acad. Sci.* USA 85:7084–7088; Zupan et al. (1992) *J. Biol. Chem.*, 267: 8707–8710; Aitken et al. (1992) *Trends. Biochem. Sci.*, 17: 498–501; Burbelo et al. (1995) *Current Biology*, 5: 95–96; Robinson et al. (1994) *Biochem. J.* 299: 853–861; Ichimura et al. (1988) *Proc. Nat'l. Acad. Sci.* USA, 85: 7084–7088; and Morgan et al. (1992) *Nature*, 355: 833–836). Assays that detect 14-3-3 are intended to detect the level of endogenous (native) 14-3-3 present in subject biological sample (e.g., CSF). However exogenous 14-3-3 (14-3-3 protein from a source extrinsic to the biological sample) may be added to various assays to provide a label or to compete with the native 14-3-3 in binding to an anti-14-3-3 antibody. One of skill will appreciate that a 14-3-3 mimetic may be used in place of exogenous 14-3-3 in this context. An "14-3-3 mimetic", as used herein, refers to a molecule that bears one or more 14-3-3 epitopes such that it is specifically bound by an antibody that specifically binds native 14-3-3.

The phrase "diagnostic of a transmissible spongiform encephalopathy" is used herein to refer to a marker or assay that is indicative of the presence or predicts the ultimate onset of a transmissible spongiform encephalopathy. However, it will be appreciated by one of skill in the art, that all assays exhibit a certain level of false positives and false negatives. Even where a positive result in an assay is not invariably associated with the ultimate onset of the encephalopathy (i.e. where there are some false positives), the result is valuable as it results in more careful monitoring of the patient or animal and the institution of appropriate containment procedures thus reducing risk of infection and transmission through the population. An assay is diagnostic of a transmissible spongiform encephalopathy where detection of the assay marker (e.g. 14-3-3 protein) shows a statistically significant association or correlation with the ultimate manifestation of symptoms of a transmissible spongiform encephalopathy (e.g., Creutzfeldt-Jacob disease in humans or mad cow disease in bovines).

The term "cerebrospinal fluid" or "CSF" as used herein includes whole cerebrospinal fluid or derivatives or fractions thereof well known to those of skill in the art. Thus a cerebrospinal fluid sample can include various fractionated forms of cerebrospinal fluid or can include various diluents as may be added to facilitate storage or processing in a particular assay. Such diluents are well known to those of skill in the art and include various buffers, preservatives and the like.

As used herein, an "immunoassay" is an assay that utilizes an antibody to specifically bind to the analyte. The immunoassay is characterized by the use of specific binding to a particular antibody as opposed to other physical or chemical properties to isolate, target, and quantify the analyte.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, W. E. Paul, ed., Raven Press, N.Y. (1993) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, antibodies can be raised to the human 14-3-3 protein that bind 14-3-3 and not to any other proteins present in a biological sample (e.g., CSF). A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

A "concentration standard" is a predetermined concentration of a particular moiety, in this case a 14-3-3 protein, that is used for standardizing an assay for that moiety. A negative control, is a sample that lacks any of the specific analyte the assay is designed to detect and thus provides a reference baseline for the assay.

DETAILED DESCRIPTION

Figure 1A:
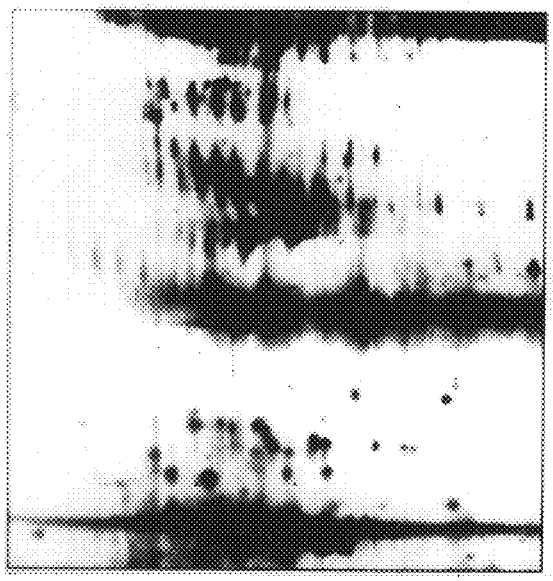
FIG. 1 shows electrophoretic isolation of 130/131 proteins. Gels "A" and "B" show a comparison between silver-stained two-dimensional electrophoresis gels of cerebrospinal fluid specimens from a control "A" and a Creutzfeldt-Jacob disease (CJD) patient "B". The CSF from patients with CJD consistently show a constellation of proteins in the area of Mr=30,000 Da and pI=5.0. For sequencing purposes, the micropreparative amounts of brain protein extract were applied to narrow range (pI 4.5–5.4) immobilized pH gradient (IPG) gels, in order to achieve a better separation of these proteins than can be obtained in analytical gels. This is illustrated by the complexity of proteins on a broad range IPG gel (gel "C"). The same region of the better-resolved brain proteins on the narrow IPG gradient is depicted shown as "D" with proteins 130/131 indicated.

I. Diagnosis of a Transmissible Spongiform Encephalopathy

This invention provides methods for the rapid detection of a transmissible spongiform encephalopathy (TSE). The transmissible spongiform encephalopathies constitute a group of neurodegenerative diseases characterized by spongiform degeneration, reactive gliosis in the cortical and subcortical gray matters of the brain, and transmission when experimentally inoculated into laboratory animals including primates, rodents, and transgenic mice. In humans these diseases include Creutzfeldt-Jakob disease (CJD), Gerstmann-Straussler-Scheinker syndrome, Fatal Familial Insomnia and Kuru. In animals the TSE's include sheep scrapie, bovine spongiform encephalopathy (mad cow disease), transmissible mink encephalopathy, and chronic wasting disease of captive mule deer and elk.

The methods of this invention generally involve detection of the presence or absence and/or quantification of a 14-3-3 protein in a biological sample, more preferably in cerebrospinal fluid (CSF). Elevated cerebrospinal fluid levels of 14-3-3 protein(s), as compared to levels characteristic of healthy controls, are taken as indicative or diagnostic of a transmissible spongiform encephalopathy (e.g., Creutzfeldt-Jacob disease in humans or mad cow disease in bovines).

The 14-3-3 proteins are a highly conserved group found in a broad range of species, including plants, yeast, Drosophila and mammals. They exist at low levels in many tissues in at least seven isoforms; however, they are most highly concentrated in the brain (see, e.g., Aitken et al. (1992) *Trends. Biochem. Sci.*, 17: 498–501). The 14-3-3 proteins seem to be involved in a wide variety of processes, including cell cycle control (Burbelo et al. (1995) *Current Biology*, 5: 95–96), regulation of protein kinase C (Robinson et al. (1994) *Biochem. J.* 299: 853–861), activation of tyrosine and tryptophan hydroxylases (Ichimura et al. (1988) *Proc. Nat'l. Acad. Sci.* USA, 85: 7084–7088), and stimulation of calcium-dependent exocytosis (Morgan et al. (1992) *Nature*, 355: 833–836).

While the 14-3-3 proteins were previously known, it was a surprising discovery of this invention that the 14-3-3 proteins are diagnostic of transmissible spongiform encephalopathies, and in particular of Creutzfeldt-Jacob disease. The diagnostic methods of this invention thus provide new uses for this previously known class of proteins.

It was previously determined, from two dimensional electrophoresis, that the protein markers designated 130 and 131 were diagnostic of transmissible spongiform encephalopathies, in humans (see, e.g., Harrington et al. (1986) *N. Engl. J. Med.*, 315: 279–283 and U.S. Pat. No. 4,892,814). In the present invention, however, it was discovered that the two protein spots designated 130 and 131 actually resolve into four to six spots. Moreover microsequencing, described herein, indicated that the subject proteins belonged to a previously known protein genus; the 14-3-3 proteins. Because of the commercial availability of anti-14-3-3, antibodies this discovery lead to the rapid and effective immunoassay for the diagnosis of transmissible spongiform encephalopathies described herein. Without recognition of the relationship between the proteins 130/131 and the 14-3-3 genus of proteins one of skill would not have appreciated that anti-14-3-3 antibodies can be used for the diagnosis of transmissible spongiform encephalopathies such as Creutzfeldt-Jacob disease.

Moreover, because the 14-3-3 proteins are widely expressed in a variety of different organisms and are highly conserved throughout their range of expression, the present discovery that 14-3-3 proteins in cerebrospinal fluid are diagnostic of transmissible spongiform encephalopathies in humans opened the possibility that, the 14-3-3 protein(s) are similarly diagnostic in cerebrospinal fluid of other species (e.g., bovines). The study described in Example 1 confirmed that elevated 14-3-3 levels in animal cerebrospinal fluids are indeed diagnostic of transmissible spongiform encephalopathies (e.g., mad cow disease).

Example 1 provides data establishing that the presence of 14-3-3 proteins in cerebrospinal fluid is a good indicator of transmissible spongiform encephalopathies both in humans and in animals. While 14-3-3 protein(s) are expressed at low levels in a number of tissues, especially brain, 14-3-3 is essentially absent from healthy cerebrospinal fluid. However, even where baseline levels of 14-3-3 are detectable in cerebrospinal fluid of healthy humans and animals, transmissible spongiform encephalopathies will be characterized by significantly elevated CSF 14-3-3 levels as compared to the healthy control.

One of skill will appreciate that, as with any assay, a certain number of false positive and false negative results will occur. The data presented herein establish that false negatives are relatively infrequent and most commonly false positive results are observed in herpes encephalitis and viral encephalitis. These diseases, however, are easily distinguished from transmissible spongiform encephalopathies on clinical presentation. For example, unlike transmissible spongiform encephalopathies, herpes and viral encephalitis do not present with dimentia. Herpes encephalitis, for example presents with acute febrile illness with immediate lapse into coma.

II. Asays for 14-3-3 proteins

As indicated above, it was a discovery of this invention that transmissible spongiform encephalopathies can be diagnosed by detection of 14-3-3 protein in cerebrospinal fluid from animals and humans. The 14-3-3 proteins can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay(RIA), enzyme-linked immunosorbent assays (ELISAs), immunofluorescent assays, western blotting, and the like.

In a particularly preferred embodiment, the 14-3-3 proteins are detected in an electrophoretic protein separation, more preferably in a two-dimensional electrophoresis, while in a most preferred embodiment, the 14-3-3 proteins are detected using an immunoassay.

As used herein, an immunoassay is an assay that utilizes an antibody to specifically bind to the analyte (14-3-3 protein). The immunoassay is thus characterized by detection of specific binding of a 14-3-3 protein to an anti-14-3-3 antibody as opposed to the use of other physical or chemical properties to isolate, target, and quantify the analyte.

The collection of biological sample and subsequent testing for 14-3-3 protein(s) is discussed in more detail below.

A) Sample Collection and Processing

The 14-3-3 proteins are preferably quantified in a biological sample derived from a mammal, more preferably from a human patient or from a bovine. As used herein, a biological sample is a sample of biological tissue or fluid that contains a 14-3-3 concentration that may be correlated with cerebrospinal levels of 14-3-3. Particularly preferred biological samples include, but are not limited to neurological tissue and cerebrospinal fluid.

The biological sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

In a preferred embodiment, assays are performed using cerebrospinal fluid (CSF). Obtaining and storing CSF are well known to those of skill in the art. Typically CSF is obtained by lumbar puncture. The CSF may be diluted by the addition of buffers or other reagents well known to those of skill in the art and may be stored for up to 24 hours at 2–8° C., or at −20° C. or lower for longer periods, prior to measurement of 14-3-3. In a particularly preferred embodiment, the CSF is stored at −70° C. without preservative indefinitely.

B) Electrophoretic Assays.

As indicated above, the presence or absence of 14-3-3 proteins in cerebrospinal fluid can be determined using electrophoretic methods. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*., Academic Press, Inc., N.Y.). In a preferred embodiment, the 14-3-3 proteins are detected using two-dimensional electrophoresis. A particularly preferred separation relies on isoelectric focusing (IEF) in immobilized pH gradients for one dimension and 14% T polyacrylamide gels for the second dimension. A detailed protocol for 14-3-3 isolation using two-dimensional electrophoresis is provided in Example 1.

Because of the lack of corresponding reference proteins in non-human organisms, identification of 14-3-3 in two-dimensional electrophoresis gels is difficult. However, 14-3-3 proteins can be routinely detected in animal CSF using the simple immunoassays described below. The 14-3-3 proteins are evolutionarily highly conserved and the anti-14-3-3 antibodies are cross-reactive among mammalian species. Thus, animal CSF 14-3-3 protein can be detected using the commercial anti-14-3-3 polyclonal antibody described below.

C) Immunological Binding Assays.

In a preferred embodiment, the 14-3-3 proteins are detected and/or quantified in CSF using any of a number of well recognized immunological binding assays (see, e.g., U.S. Pat. Nos. 4,366,241; 4,376,110; 4,517,288; and 4,837, 168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991).

Immunological binding assays (or immunoassays) typically utilize a "capture agent" to specifically bind to and often immobilize the analyte (in this case 14-3-3). The capture agent is a moiety that specifically binds to the analyte. In a preferred embodiment, the capture agent is an antibody that specifically binds 14-3-3 protein(s).

The antibody (anti-14-3-3) may be produced by any of a number of means well known to those of skill in the art (see, e.g. *Methods in Cell Biology Volume 37: Antibodies in Cell Biology*, Asai, ed. Academic Press, Inc. New York (1993); and *Basic and Clinical Immunology* 7th Edition, Stites & Terr, eds. (1991)). The antibody may be a whole antibody or an antibody fragment. It may be polyclonal or monoclonal, and it may be produced by challenging an organism (e.g. mouse, rat, rabbit, etc.) with a 14-3-3 protein or an epitope derived therefrom. Alternatively, the antibody may be produced de novo using recombinant DNA methodology. The antibody can also be selected from a phage display library screened against 14-3-3 (see, e.g. Vaughan et at. (1996) *Nature Biotechnology*, 14: 309–314 and references therein).

Anti-14-3-3 antibodies can also be obtained commercially. For example, Santa Cruz Biotechnology (Santa Cruz, Calif.) manufactures a polyclonal antibody directed against human 14-3-3 (Catalogue number sc-629). This polyclonal antisera is species cross-reactive and capable of specifically binding to animal (e.g., bovine) 14-3-3 in CSF preparations.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled 14-3-3 protein or a labeled anti-14-3-3 antibody. Alternatively, the labeling agent may be a third moiety, such as another antibody, that specifically binds to the antibody/14-3-3 complex.

In a preferred embodiment, the labeling agent is a second human 14-3-3 antibody bearing a label. Alternatively, the second 14-3-3 antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species. See, generally Kronval, et al., *J. Immunol.*, 111:1401–1406 (1973), and Akerstrom, et al., *J. Immunol.*, 135:2589–2542 (1985).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

1) Non-Competitive Assay Formats.

Immunoassays for detecting CSF 14-3-3 protein may be either competitive or noncompetitive. Noncompetitive immunoassays are assays in which the amount of captured analyte (in this case 14-3-3) is directly measured. In one preferred "sandwich" assay, for example, the capture agent (anti-14-3-3 antibodies) can be bound directly to a solid substrate where they are immobilized. These immobilized antibodies then capture 14-3-3 present in the test sample. The 14-3-3 thus immobilized is then bound by a labeling agent, such as a second human 14-3-3 antibody bearing a label. Alternatively, the second 14-3-3 antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats.

In competitive assays, the amount of analyte (14-3-3) present in the sample is measured indirectly by measuring the amount of an added (exogenous) analyte (14-3-3) displaced (or competed away) from a capture agent (anti 14-3-3 antibody) by the analyte present in the sample. In one competitive assay, a known amount of, in this case, 14-3-3 is added to the sample and the sample is then contacted with a capture agent, in this case an antibody that specifically binds 14-3-3. The amount of 14-3-3 bound to the antibody is inversely proportional to the concentration of 14-3-3 present in the sample.

In a particularly preferred embodiment, the antibody is immobilized on a solid substrate. The amount of 14-3-3 bound to the antibody may be determined either by measuring the amount of 14-3-3 present in an 14-3-3/antibody complex, or alternatively by measuring the amount of remaining uncomplexed 14-3-3. The amount of 14-3-3 may be detected by providing a labeled 14-3-3 molecule.

A hapten inhibition assay is another preferred competitive assay. In this assay a known analyte, in this case 14-3-3 is immobilized on a solid substrate. A known amount of anti-14-3-3 antibody is added to the sample, and the sample is then contacted with the immobilized 14-3-3. In this case, the amount of anti-14-3-3 antibody bound to the immobilized 14-3-3 is inversely proportional to the amount of 14-3-3 present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Other Assay Formats

In a particularly preferred embodiment, Western blot (immunoblot) analysis is used to detect and quantify the presence of 14-3-3 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind 14-3-3. The anti-14-3-3 antibodies specifically bind to 14-3-3 on the solid support. These antibodies may be directly labeled or alternatively may be subsequently detected using labeled antibodies (e.g., labeled sheep anti-mouse antibodies) that specifically bind to the anti-14-3-3. A particularly preferred protocol for Western Blot detection of human or animal 14-3-3 protein in CSF is provided in Example 1.

Other assay formats include liposome immunoassays (LIA), which use liposomes designed to bind specific mnolecules (e.g., antibodies) and release encapsulated reagents or markers. The released chemicals are then detected according to standard techniques (see, Monroe et al. (1986) *Amer. Clin. Prod. Rev.* 5:34–41).

D) Scoring of the Assay.

The assays of this invention as scored (as positive or negative for 14-3-3 protein) according to standard methods well known to those of skill in the art. The particular method of scoring will depend on the assay format and choice of label. For example, the Western Blot assay illustrated in Example 1 is scored by visualizing the colored product produced by the enzymatic label. A clearly visible colored band or spot at the correct molecular weight (30 kDa) was scored as a positive result, while the absence of a clearly visible spot or band was scored as a negative. In a preferred embodiment, a positive test will show a signal intensity (e.g., 14-3-3 protein quantity) at least twice that of the background and/or control and more preferably at least 3 times or even at least 5 times greater than the background and/or negative control.

E) Reduction of Non-Specific Binding.

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

F) Labels.

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabead™), fluorescent dyes (e.g., fluorescein isothiocyanate, texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

G) Substrates.

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas (1970) *J. Biol. Chem.* 245 3059).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

III. Determination of 14-3-3 Levels for Diagnosis of Transmissible Spongiform Encephalopathies This invention is premised, in part, on the surprising discovery that transmissible spongiform encephalopathies are associated with elevated levels of 14-3-3 protein(s) in cerebrospinal fluid as compared to the cerebrospinal fluid sample from a healthy control organism.

The CSF levels of 14-3-3 may vary with the physiological state of the patient (human or animal). Variables that can effect CSF levels can include age of the organism, infections (e.g., herpes encephalitis, viral encephalitis, etc.) and the like. Nevertheless, baseline healthy levels of cerebrospinal fluid 14-3-3 and levels indicative of transmissible spongiform encephalopathies (e.g, Creutzfeldt-Jacob disease or bovine spongiform encephalopathy) may be determined by means well known to those of skill in the art. Generally this simply involves assaying healthy patients (or animals) and patients (or animals) that ultimately develop transmissible spongiform encephalopathies to determine cerebrospinal fluid levels of 14-3-3 characteristic of the healthy and diseased state.

IV. Diagnostic Kits for Detection or Prediction of Transmissible Spongiform Encephalopathies The present invention also provides for kits for the detection of transmissible spongiform encephalopathies in humans or animals (e.g., bovines). The kits preferably include an antibody that specifically binds to 14-3-3. The antibody may be monoclonal or polyclonal and can be free or immobilized on a solid support such as a test tube, a microtiter plate, a dipstick and the like. The kit may also contain instructional materials teaching the use of the antibody in an assay for the diagnosis of transmissible spongiform encephalopathies (e.g., Creutzfeldt-Jacob disease or bovine spongiform encephalopathy).

Additionally, the kit may contain a second antibody that specifically binds 14-3-3 or that binds an anti-14-3-3 antibody. The second antibody may be labeled, or alternatively, the kit may contain a labeled third antibody that specifically binds the second antibody. The kit can also contain 14-3-3 protein(s) immobilized on a solid support. The kit may also contain appropriate control series of 14-3-3, buffer solutions, positive and negative controls, washing solutions, dilution buffers and the like for the preparation and analysis of 14-3-3 in blood.

One particularly preferred kit provides components for detection of 114-3-3 proteins using a sandwich assay. The kit provides immobilized anti-14-3-3 antibody, 14-3-3 concentration standards, fluorescently, radioactively or enzymatically labeled anti-14-3-3, and positive and negative 14-3-3 controls. As described above, the immobilized anti-14-3-3 specifically binds to 14-3-3 present in the sample. Then the labeled anti-14-3-3 binds to the already bound 14-3-3. Free labeled anti-14-3-3 is washed away and the remaining bound labeled anti-14-3-3 is detected using a detection system appropriate to the particular label (e.g., a gamma detector for a radioactive label, visual inspection or video data acquisition system for fluorescent label).

EXAMPLES

The following examples are offered to illustrate, but not to limit the present invention.

Example 1

Methods

Patients and Animals

Cerebrospinal fluid (CSF) samples consisted of referrals from various neurological centers around the world to the Laboratory of Central Nervous System Studies, National Institute of Neurological Disorders and Stroke. For Creutzfeldt-Jakob disease (CJD), patients comprised three categories: One category had neuropathological confirmation of disease on follow-up. The "clinically definite" category consisted of cases strongly suggestive of CJD by clinical history, including a rapidly progressive dementia, myoclonus, and a characteristic EEG (Brown et al. (1986) Annals. Neurol. 20: 597–602). The patients with the "probable and possible" criteria of Brown et al., included cases with rapidly progressive dementia and one of the following: myoclonus, movement disorder, or periodic EEG (Brown et al. (1986) Annal. Neurol. 20: 597–602) and were also required to have detectable CSF 130/131 by two-dimensional electrophoresis (Harrington et al. (1986) N. Engl. J. Med., 315: 279–283) to be included in this study as "probable" CJD. Alzheimer's disease patients fell into two groups. One had neuropathological confirmation of disease on follow-up, while the other had criteria for "clinically definite" disease (McKhann (1984) Neurol. 34: 939–944).

Sample Preparation

All samples were stored at −70° C. without preservative. Non-CJD human rain tissue was prepared by homogenizing one part brain into five parts of a solution containing 8 M urea, 1.5 M Tris pH 8, and 0.5% sodium dodecyl sulfate (SDS). This preparation was then sonicated in a cold water bath until the mixture was completely liquefied and homogenous (about 30 minutes). β-mercaptoethanol was added to yield a final 0.1% (v/v). The samples, 200 μl each of cerebrospinal fluid or brain extract, were concentrated by acetone precipitation, and then reconstituted in 100 μl solution of 9.67 M urea, 5% ([3-chol-amido-propyl)-dimethyl[-ammonio]-1propane sulfonate, 6% carrier ampholytes, 2% DTE, 40 mM Tris.

Two-dimensional Electrophoresis (2DE)

Two dimensional electrophoresis consisted of isoelectric focusing followed by electrophoresis using a polyacrylamide gel. Isoelectric focusing (IEF) was done in immobilized pH gradients. The 180 mM linear pH 3–10 gradient (Pharmacia LKB, Piscataway, N.J., USA, catalog #17-1234-01) or the Immobiline DryPlate pH 4.5–5.4 (Pharmacia, catalog #80-1128-30) were used. These gradients were rehydrated, electrophoresed, and equilibrated as described in (Bjellqvist et al. (1993) Electrophoresis, 14: 1375–1378; and Bjellqvist et al. (1993) Electrophoresis, 14: 1357–1365). The second dimension was performed in 14% T polyacrylamide gels and silver stained (see Harrington et al. (1991) methods: A Companion to Methods in Enzymology, 3: 98–108) or electroblotted (Towbin et al. (1979) Proc. Nat'l. Acad. Sci, 76: 4350–4354) onto nitrocellulose (Schleicher & Schuell, catalog # 0830N) or PVDF (Millipore, Mass., USA). The blots were stained with Coomassie Brilliant Blue R-250. Two-dimensional electrophoresis gels and blots were analyzed either by direct visual comparison, by comigration studies, and/or with the aid of computer image analysis software. GALtool (Solomon et al. (1993) CABIOS 9: 133–139).

Protein Sequencing

Protein spots of interest were excised from nitrocellulose blots by the method of Aebersold et al. (Aebersold et at. (1987) Proc. Nat'l. Acad. Sci., 84: 6970–6974). Individual spots from 10 blots were combined, digested with Lysyl endopeptidase (Wako Bioproducts, Virgina, USA, catalog # 129-02541), and eluted from the nitrocellulose. Peptide fragments were separated by reverse-phase HPLC (RPC C2/C18, PC 3.2/3, Pharmacia LKB, Piscataway, N.J., USA) and amino acid sequences determined with the aid of an ABI 477 microsequencer (Perkin Elmer/Applied Biosystems Division, Foster City, Calif., USA). Amino acid sequences were compared to the Swiss-Prot data bank, using the BLAST program at http://www.ncbi.nlm.nih.gov.

Screening CSF Proteins 130/131 with Specific Antisera

Antisera were evaluated for their immunoreactivity against CSF 130/131 on a 2DE Western blot on PVDF (Millipore) of CSF proteins from a patient with CJD. Total protein was first visualized with colloidal gold (BioRad, Hercules, Calif., USA)). The blot was subsequently immunostained using a chemilluminescent substrate (Pierce Chemical Co., Illinois, USA, catalog # 34080) to detect and localize the antigen.

Immunoassay of CSF

The immunostain was adapted from published protocols (Brown et al. (1986) N. Engl. J. Med., 314: 547–551) and optimized using specimens of known diagnosis. Each CSF sample (50 μl) was mixed with 10 μl of sample buffer (5% glycerol, 1% β-mercaptoethanol, 1% SDS, and a trace of Bromophenol blue in final solution) and boiled for 5 minutes. This sample was subject to SDS-polyacrylamide gel electrophoresis (SDS-PAGE) in 4% T stacking/12% T resolving gels at 75 V for about 3–4 hours and then electrotransferred to nitrocellulose (Towbin (1979) supra.).

Immunostaining of the membrane was performed by first blocking with Tris buffered saline solution with 0.3% Tween for 30 minutes, incubation with anti-14-3-3 polyclonal rabbit primary antibody (Toshiaki Isobe of Tokyo Metropolitan University; and Santa Cruz Biotechnology, Calif., catalog #sc-629) at a dilution of 1:500, and then with a human adsorbed, alkaline phosphatase-conjugated secondary antibody (Biosource, International, Camarillo, Calif., USA) at a dilution of 1:1000. Antigen was detected by colorimetric reaction. Biotinylated molecular weight markers and a positive control (CSF from a CJD-positive patient) were run on every gel.

A clearly visible colored band or spot at the correct molecular weight (30 kDa) was scored as a positive result, while the absence of a clearly visible spot or band was scored as a negative.

Immunoassay Analysis

The immunoassay (14-3-3 assay) results were scored as positive or negative independent of the diagnosis. Statistical significance was calculated using 2×2 contingency tables (Fleiss Statistical methods for rates and proportions. (1981) John Wiley and Sons New York). P values<0.05 were considered significant.

Results

Identification of Proteins 130/131

Figure 1B:
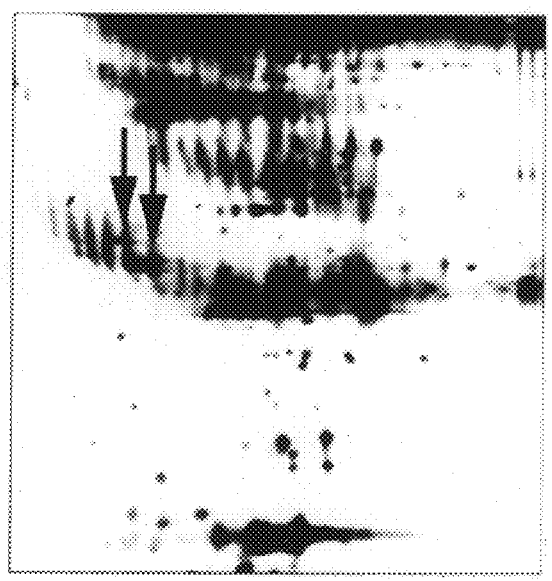
Figure 1C:
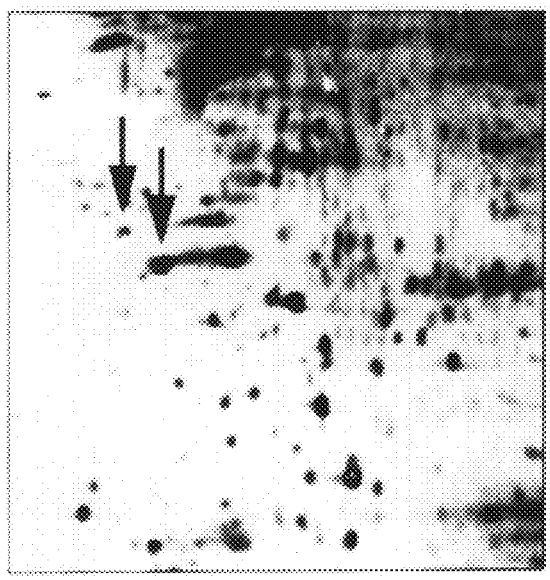
Figure 1D:
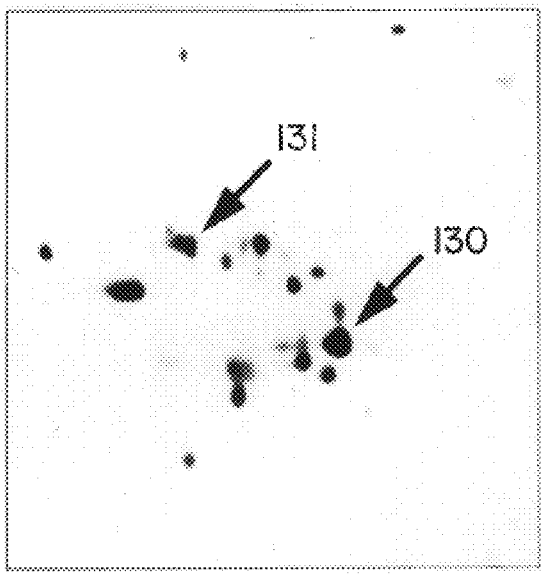

The association of CSF proteins 130 and 131 with Creutzfeldt-Jakob disease (CJD) was first verified. FIG. 1, gels "A" and "B" show a comparison between silver-stained two-dimensional electrophoresis gels of cerebrospinal fluid specimens from a control (gel "A") and a CJD patient (gel "B"). The CSF from patients with CJD consistently show a constellation of proteins in the area of Mr=30,000 Da and pI=5.0. This constellation included the proteins 130 and 131 first observed by Harrington et al., (1986) *N. Engl. J. Med.*, 315: 279–283 (see also U.S. Pat. No. 4,892,814).

However, in the present experiment, improvements in the resolution and reproducibility of the two-dimensional electrophoresis result in the appearance of a cluster of four to six spots rather than the two spots originally described. These proteins are not seen in the CSF of patients with other neurological diseases, even when significantly more total protein is loaded onto the gels.

In order to locate an abundant source of these proteins, normal brain tissue was examined to determine whether any brain proteins co-localized to the same area as CSF proteins 130/131. Gel "C" in FIG. 1 is a silver-stained two-dimensional electrophoresis gel of brain proteins. Several brain proteins appeared in the same area as the 130/131 constellation, including two that have the same charge/mass position as the CSF proteins (indicated by the arrows on gel "C") as determined by GALtool image analysis software (Solomon et al. (1993) supra.). In order to further check the co-localization between the CSF 130/131 and the brain proteins, a mixture of the extract of normal brain proteins and CSF proteins from a CJD patient was analyzed by two-dimensional electrophoresis. The brain spot that localized with CSF 130 increased in the electrophoreses gel of this mixture, further suggesting that this brain protein was the same as the CSF 130 protein.

Amino acid Microsequencing of Proteins 130/131

For sequencing purposes, micropreparative amounts of brain protein extract were applied to narrow range (pI 4.5–5.4) immobilized pH gradient (IPG) gels, in order to achieve a better separation of these proteins than can be obtained in analytical gels. This is illustrated by the complexity of proteins on the broad range IPG gel shown in the inset box in FIG. 1, gel "C". The same region of the better-resolved brain proteins on the narrow IPG gradient is depicted in FIG. 1, gel "D", with proteins 130/131 indicated. These were transferred to nitrocellulose and stained with Coommassie Blue.

The spots corresponding to protein 130 were excised from 10 blots, enzymatically digested, and peptides were purified and microsequenced. Sequence was obtained from four peptide fragments, with an initial yield of 4±2 picomoles. Three of these peptides, VTELNEPLXNEDXNLLSVA (SEQ ID NO:1), DYYXYLAEVATGEK (SEQ ID NO:2), and NVVXARRSSXRVISSIEQ (SEQ ID NO:3) match the human sequence of the 14-3-3 protein, 143F_human, Swiss-Prot Accession #QO4917. The fourth sequence, YSE-AXEIS (SEQ ID NO:4), matches the bovine 143G_bovin, Swiss-Prot Accession #P29359.

To verify the identity of CSF proteins 130/131 as 14-3-3 proteins, a two-dimensional electrophoresis blot of CSF from a CJD patient was stained twice as described above in the methods section. First, total CSF proteins (including 130/131) were detected with colloidal gold; next, the blot was immunostained with the anti-14-3-3 antibody. This antibody stained two spots that superimposed the gold stained proteins 130/131. The control CSF lacked the 130/131 constellation and showed no reaction against the anti-14-3-3 antibodies.

Immunoassay

The discovery that proteins 130/131 are 14-3-3 proteins has resulted in a fast, simple, and reliable test to aid in the diagnosis of CJD (Table 1). 14-3-3 immuno-reactivity is not detected in CSF from normal persons while it is detected clearly in CSF from patients with CJD. No 14-3-3 immunoreactivity was observed with scrapie-infected hamster brain, and purified scrapie-associated fibrils, while these extracts were strongly immunoreactive for the PrP 3F4 antibody. To determine whether 14-3-3 proteins exist in the peripheral circulation, sera from both CJD and non CJD patients were evaluated and neither showed immunoreactivity under these assay conditions.

Specificity and Sensitivity of 14-3-3 Immunoassay for Human CJD

Of the Creutzfeldt-Jacob diseased CSF specimens, 52 of 55 (94.5%) were positive in the 14-3-3 assay (Table 1). These cases involve three levels of diagnostic confidence: pathologically positive (21/24), clinically definite (10/10), or clinically probable/possible and positive in two-dimensional electrophoresis (21/21). In the three cases which were pathologically positive for CJD, but negative for the 14-3-3 marker the immunoassay did show a reaction, but the results were not as clear as other specimens which were positive for 14-3-3. Only 1 of 71 specimens from patients with dementing diseases were positive for the 14-3-3 protein (1.4%). This was a weak positive from a patient with Alzheimer's disease. Of 34 specimens from patients with other, non-dementing neurological illnesses one was positive, from a patient with Rett's syndrome. In total, the 14-3-3 immunoassay test for CJD among clinically demented patients had a sensitivity of >94% ($p<0.001$) and a specificity of >98% ($p<0.001$).

TABLE 1

Summary of 14-3-3 western blot test for human cerebrospinal fluid.

| Diagnosis | Total Patients | 14-3-3 positive |
|---|---|---|
| Creutzfeldt-Jakob disease: | | |
| Pathologically positive | 24 | 21 |
| Clinically definite[1] | 10 | 10 |
| Clinically probable[2] and 130/131 positive | 21 | 21 |
| Total CJD (94.5%) | 55 | 52 |
| Encephalitis: | | |
| Herpes (91.7%) | 12 | 11 |
| Other viral (11.1%) | 9 | 1 |
| Total encephalitis | 21 | 12 |
| Neurological Disorders: | | |
| Dementias | | |
| Alzheimer's (Pathologically positive) | 31 | 0 |
| Alzheimer's (Clinically positive.)[3] | 16 | 1 |
| Suspected CJD, but 130/131 negative | 12 | 0 |
| CNS Lymphoma | 1 | 0 |
| Cortical Basal Ganglionic Degeneration | 1 | 0 |
| Metabolic encephalopathy | 1 | 0 |
| Normal Pressure Hydrocephalus | 6 | 0 |
| Parkinson's disease with Dementia | 2 | 0 |
| Other (pathologically CJD negative) | 1 | 0 |
| Total Non-CJD Dementia (1.4%) | 71 | 1 |
| Non-Dementias | | |
| Amyotiophic lateral sclerosis | 3 | |
| Chronic Inflam. Demyolinating Polyradiculopathy | 1 | 0 |
| Headache | 7 | 0 |
| Multiple Sclerosis | 5 | 0 |
| Neurosyphilis | 1 | 0 |
| Parkinson's Disease | 3 | 0 |

TABLE 1-continued

Summary of 14-3-3 western blot test for human cerebrospinal fluid.

| Diagnosis | Total Patients | 14-3-3 positive |
|---|---|---|
| Pseudotumor Cerebri | 2 | 0 |
| Psychiatric | 2 | 0 |
| Rasmussen's Encephalitis | 1 | 0 |
| Rett's Syndrome | 5 | 1 |
| Schilder's | 1 | 0 |
| Subacute Sclerosing Panencephalitis | 3 | 0 |
| Total Non-Dementia Diseases (2.9%) | 34 | 1 |
| Normal | 2 | 0 |
| TOTAL NON-CJD (1.9%) | 107 | 2 |

1 Rapidly progressive dementia, myoclonus, and characteristic EEG findings of triphasic, periodic sharp waves (Brown et al. (1986) supra.).
2 Rapidly progressive dementia and one of the following: myoclonus, movement disorder, or periodic EEG (Brown et al. (1986) supra.).
3 McKhann et al. (1984) (supra).

Comparison of Two-dimensional Electrophoresis and Immunoassay

In a comparison of the two-dimensional electrophoresis and the immunoassay, 69 cerebrospinal fluid specimens were tested by both methods. As shown in Table 2, 34 of the 36 specimens from patients with CJD were positive by both two-dimensional electrophoresis and the 14-3-3 immunoassay (Western Blot). The remaining two specimens were negative by two-dimensional electrophoresis, but positive by 14-3-3 immunoassay. Of the samples from patients with dementias and other neurological disorders, 32 of 33 were negative by both 130/131 (electrophoresis) and the 14-3-3 immunoassay; one was positive only in the 14-3-3 immunoassay, a patient with Rett's syndrome whose two-dimensional electrophoresis showed extensive protein degradation. As evidenced by the data in Table 2, there is close correlation between the two tests, but the 14-3-3 immunoassay of this invention has increased sensitivity and slightly decreased specificity compared to the two-dimensional electrophoresis test for proteins 130/131.

Because spots 130/131 have also been found in herpes encephalitis, 21 cases of encephalitis, 12 of which were either culture or polymerase chain reaction (PCR) positive for herpes simplex, and 9 of which were acute viral encephalitides of non-herpes origin, were also tested. Of the 12 herpes cases, 11/12 (92%) were 14-3-3 positive and 1/9 (11%) of the non-herpes encephalitides were 14-3-3 positive.

TABLE 2

Concordance between two-dimensional electrophoresis and 14-3-3 immunoassay.

| Diagnosis | Total # tested | Electrophoresis Positive | 14-3-3 Immunoassay Positive |
|---|---|---|---|
| Creutzfeldt-Jakob Disease | | | |
| Positive Pathology | 5 | 5 | 5 |
| Clinically Definite[1] | 10 | 8 | 10 |
| Clinically Probable[2] | 21 | 21 | 21 |
| Total CJD | 36 | 34 | 36 |
| Non-Creutzfeldt-Jakob | | | |
| Dementias | 18 | 0 | 0 |
| Other Disorders | 13 | 0 | 1 |
| Normal | 2 | 0 | 0 |

TABLE 2-continued

Concordance between two-dimensional electrophoresis and 14-3-3 immunoassay.

| Diagnosis | Total # tested | Electrophoresis Positive | 14-3-3 Immunoassay Positive |
|---|---|---|---|
| Total NON-CJD | 33 | 0 | 1 |

1 Rapidly progressive dementia, myoclonus, and characteristic EEG findings of triphasic, periodic sharp waves (Brown et al. (1986) supra.).
2 Rapidly progressive dementia and one of the following: myoclonus, movement disorder, or periodic EEG. (Brown et al. (1986) supra.).

14-3-3 Immunoassay for Animal TSE

The discovery of the 14-3-3 identity of proteins 130/131 enables this direct identification in animal CSF without the need for several reference proteins. As the 14-3-3 proteins are evolutionarily highly conserved and the antibodies are cross-reactive among species, animal CSF 14-3-3 protein was studied using the same commercial polyclonal antibody (Santa Cruz Biotechnology, Santa Cruz, Calif., USA, catalog # sc-629 and sc-731).

The results from animal studies (see Table 3) are consistent with the 14-3-3 marker reflecting TSE pathology. All "control" cows, sheep and the chimpanzee studies had no detectable 14-3-3 protein, while most of the pathologically inoculated animals (11/15) had 14-3-3 in the CSF. There was one positive in a cow that had been inoculated with scrapie, but was not pathologically positive for bovine spongiform encephalopathy.

TABLE 3

Summary of 14-3-3 immunoassay of animal cerebrospinal fluid.

| Diagnosis | Total No. of Specimens | Number of CSFs with 14-3-3 |
|---|---|---|
| COWS | | |
| Cows inoculated with TME | 5 | 3 |
| Positive pathology | 1 | 1 |
| Negative pathology | | |
| Cows inoculated with scrapie | | |
| Positive pathology | 4 | 3 |
| Normal | 2 | 0 |
| SHEEP | | |
| Positive pathology | 5 | 4 |
| Normal control | 1 | 0 |
| CHIMPANZEES | | |
| Positive pathology | 1 | 1 |
| Negative pathology | 1 | 0 |

Discussion

The above-described experiments show that the 14-3-3 proteins are highly sensitive and specific markers for CJD and for other transmissible spongiform encephalopathies. This discovery has been incorporated into a simple immunoassay test for Creutzfeldt-Jakob disease, thereby eliminating the necessity for the cumbersome and time-consuming two-dimensional electrophoresis process in diagnosing CJD and other transmissible spongiform encephalopathies. In addition to simplifying the detection method for these proteins, interpretation of results is more objective.

This new 14-3-3 test is useful in differentiating CJD from other dementing illnesses. Only one of forty-seven (2%)

cases of Alzheimer's disease was positive for 14-3-3 proteins. The only false positive results were observed with herpes encephalitis and in a single case of Rett's syndrome. However, these diseases are easily distinguished from CJD on clinical presentation.

The role of 14-3-3 proteins in the pathophysiology of Creutzfeldt-Jakob disease is yet to be determined. With regard to the spongiform encephalopathies, an intriguing function of 14-3-3 proteins is their possible role in the conformational stabilization of proteins since a presently uncharacterized molecular chaperone may be intimately involved in the conversion of normal prion protein into the abnormal conformation (Telling et al.(1995) *Cell*, 83: 79–80). Several reports indicate that 14-3-3 proteins may activate Raf-1 activity in the Ras signal transduction pathway by altering or stabilizing the conformation of the Raf protein (Freed et al. (1994) *Science* 265: 1713–1715; Fantl et al. (1994) *Nature*, 371: 612–614; Irie et al. (1994) *Science* 265: 1716–1719; Morrison (1994) *Science*, 266: 56–57). The 14-3-3 proteins may thus play a mechanistic role in prion pathology.

In summary, the previously reported cerebrospinal fluid marker proteins 130 and 131 of Creutzfeldt-Jakob disease are identified herein as 14-3-3 proteins. This discovery permitted the development of a simple immunoassay test for CJD, and this new procedure shows high sensitivity and specificity for CJD in the context of clinical dementia. Furthermore, the same immunoassay provides a good indicator of TSE in animals. This test can now be more widely used to differentiate CJD from other dementing illnesses, such as Alzheimer's disease and reduce the need for brain biopsy.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of detecting a transmissible spongiform encephalopathy in a non-human mammal, said method comprising detecting a 14-3-3 protein in cerebrospinal fluid of said non-human mammal, wherein an elevated level of said 14-3-3 protein is indicative of said transmissible spongiform encephalopathy.

2. The method of claim 1, wherein said detecting of said 14-3-3 protein is by two-dimensional electrophoresis.

3. The method of claim 1, wherein said detecting of said 14-3-3 protein is by an immunoassay.

4. The method of claim 3, wherein said immunoassay uses an anti-14-3-3 antibody.

5. The method of claim 4, wherein said antibody is polyclonal.

6. The method of claim 5, wherein said immunoassay is a Western Blot assay.

7. The method of claim 1, wherein said non-human mammal is a bovine.

8. The method of claim 1, wherein said transmissible spongiform encephalopathy is bovine spongiform encephalopathy (mad cow disease).

9. The method of claim 1, wherein said non-human mammal is a sheep.

10. The method of claim 1, wherein said transmissible spongiform encephalopathy is sheep scrapie.

* * * * *

UNITED STATES PATENT AND TRADEMARK OFFICE
CERTIFICATE OF CORRECTION

PATENT NO. : 5,998,149
DATED : December 7, 1999
INVENTOR(S) : Hsieh et al.

It is certified that error appears in the above-identified patent and that said Letters Patent is hereby corrected as shown below:

On the cover page at [73], Assignee, insert -- and California Institute of Technology, Pasadena, CA --.

Signed and Sealed this

Sixth Day of February, 2001

Attest:

Attesting Officer

Q. TODD DICKINSON
Director of Patents and Trademarks

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Val Thr Glu Leu Asn Glu Pro Leu Xaa Asn Glu Asp Xaa Asn Leu Leu
1          5                  10                15

Ser Val Ala (2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Asp Tyr Tyr Xaa Tyr Leu Ala Glu Val Ala Thr Gly Glu Lys
1          5                  10

(2) INFORMATION FOR SEQ ID NO:3:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Asn Val Val Xaa Ala Arg Arg Ser Ser Xaa Arg Val Ile Ser Ser Ile
1               5                   10                  15

Glu Gln (2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Tyr Ser Glu Ala Xaa Glu Ile Ser
1               5
```